United States Patent [19]

Fischer

[11] 4,188,341
[45] Feb. 12, 1980

[54] PROCESS FOR THE PRODUCTION OF (SUBSTITUTED) 2,6-DIMETHYLANILINES

[75] Inventor: Hanspeter Fischer, Bottmingen, Switzerland

[73] Assignee: Ciba-Geigy Corporation, Ardsley, N.Y.

[21] Appl. No.: 923,608

[22] Filed: Jul. 11, 1978

Related U.S. Application Data

[63] Continuation-in-part of Ser. No. 759,144, Jan. 13, 1977, abandoned, which is a continuation-in-part of Ser. No. 632,744, Nov. 17, 1975, abandoned.

[51] Int. Cl.$^2$ ...................... C07C 85/06; C07C 85/08
[52] U.S. Cl. .................................... 260/573; 260/577; 260/578
[58] Field of Search ............... 260/573, 577, 578, 581, 260/574

[56] References Cited

U.S. PATENT DOCUMENTS

| | | | |
|---|---|---|---|
| 3,219,704 | 11/1965 | Wilder et al. | 260/576 |
| 3,857,892 | 12/1974 | Wehrli | 260/586 R |

OTHER PUBLICATIONS

Fieser and Fieser, "Reagents for Organic Synthesis", p. 621 (1967).

Sidgwick, "The Organic Chemistry of Nitrogen", p. 133 (1966).

Morrison and Boyd, "Organic Chemistry", Third Edition, p. 740 (1974).

*Primary Examiner*—John Doll
*Attorney, Agent, or Firm*—Karl F. Jorda

[57] ABSTRACT

Aniline derivatives of the formula

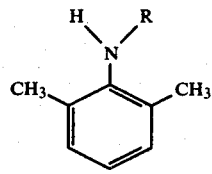

wherein R is hydrogen, $C_1$–$C_4$-alkyl or $C_1$–$C_4$-alkyl substituted by $C_1$–$C_2$-alkoxy are produced by reacting a N-(3-pent-2-enyl)-derivative of morpholine, piperidine or pyrrolidine with acrolein in the presence of an inert, aprotic solvent or in the absence of a solvent and heating the reaction product obtained to 100°–400° C. in the presence of a hydrogen-transfer catalyst and in the presence of an amine of the formula R—$NH_2$, wherein R has the meaning given above.

8 Claims, No Drawings

PROCESS FOR THE PRODUCTION OF (SUBSTITUTED) 2,6-DIMETHYLANILINES

CROSS-REFERENCE TO RELATED APPLICATIONS

This application is a continuation-in-part of my application Ser. No. 759,144, filed Jan. 13, 1977, which in turn is a continuation-in-part of Ser. No. 632,744, filed Nov. 17, 1975, both now abandoned.

The present invention relates to a process for the production of aniline derivatives of the formula I

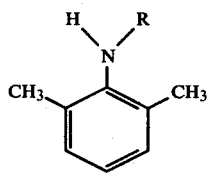

wherein

R represents hydrogen, $C_1$–$C_4$-alkyl or $C_1$–$C_4$-alkyl substituted by $C_1$–$C_2$-alkoxy.

Substituted anilines of the formula I can be used as intermediates for producing halogenoacetanilides, which for their part, by virtue of their biological action, can be employed for the regulation of plant growth and for the control of phytopathogenic fungi. Such halogenoacetanilides and their use for the regulation of plant growth and their use for the control of phytopathogenic fungi are described in British Pat. Nos. 1.422.473; 1.445.378 and 1.448.810.

It is known how aromatic amines can be produced from corresponding phenols by reaction with ammonia in the presence of a hydrogen-transfer catalyst and in the presence of small amounts of a cyclohexanone that corresponds to the phenol (see DT-OS No. 2,208,827, British Pat. No. 1,344,574). A disadvantage of this process is that it is necessary to use aromatic starting materials, which are expensive as a result of the growing scarcity of aromatic raw materials.

There is moreover known from the U.S. Pat. No. 3,857,892 a process in which 2,3,6-trialkylphenols are produced from aliphatic starting materials by reacting an α,β-unsaturated aldehyde with a dialkylketone in the presence of a base to the corresponding 2,3,6-trialkyl-2-cyclohexenone, and dehydrogenating this in the presence of a hydrogen-transferring catalyst. This process however yields satisfactory yields only for 2,3,6-trialkylphenols, whilst in an analogous manner 2,6-dialkylphenols are obtained only in moderate yield. This process therefore is able to cover the requirement for alkylphenols as starting materials for the production of aromatic amines only to an inadequate degree.

It is therefore the object of the present invention to provide a process that renders possible, in a simple manner and in good yields, the production of aniline derivatives of the formula I from aliphatic starting materials.

According to the present invention, it is suggested that aniline derivatives of the formula I be produced by a process in which an enamine of the formula II

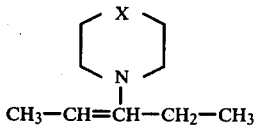

wherein X represents a methylene group, oxygen or a direct bond, is reacted at a temperature of between −30° C. and 150° C. with acrolein in the presence of an inert aprotic solvent, and the reaction product obtained is subsequently heated to a temperature of between 100° and 400° C. in the presence of a hydrogen-transfer catalyst and in the presence of an amine of the formula III

R—NH$_2$ wherein R has the meaning given under formula I.

The reaction of an enamine of the formula II with acrolein can be performed in an inert aprotic solvent or in the absence of a solvent. Suitable solvents are ethers such as diethyl ether, tetrahydrofuran or dioxane, aliphatic hydrocarbons such as hexane, chlorinated aliphatic hydrocarbons such as methylene chloride, chloroform, carbon tetrachloride or 1,2-dichloroethane, aromatic hydrocarbons such as benzene or toluene. The dehydrogenation in the presence of an amine of the formula III can be performed in an aqueous medium, or in an organic solvent such as tetrahydrofuran or dioxane, or in an aromatic hydrocarbon such as benzene or toluene.

After the reaction of an enamine of formula II with acrolein there can be advantageously added to the reaction mixture anhydrous acids such as hydrogen chloride, sulphuric acid, phosphoric acid, sulfonic acids, for example p-toluenesulfonic acid and methanesulfonic acid, carboxylic acids, for example acetic acid, or a salt of an amine of formula III with one of the afore-mentioned acids.

Suitable hydrogen-transfer catalysts are, in particular, platinum and palladium, especially palladium or charcoal.

An advantageous embodiment of the process of the invention comprises a procedure whereby an enamine of the formula II is reacted with acrolein and the reaction product obtained is converted by the addition of acid into 2,6-dimethyl-2-cyclohexen-1-one which is then converted by further reaction with an amine of the formula III, in the presence of a hydrogen-transferring catalyst, into a aniline of the formula I. The acid employed can be, in particular, hydrogen chloride or sulphuric acid. The acid can be used in anhydrous form or in the form of an aqueous solution.

A further advantageous embodiment of the process of the invention comprises a procedure whereby the reaction product formed by reaction of an enamine of the formula II with acrolein is reacted, firstly with an amine of the formula III and the product formed is subsequently dehydrogenated, in the presence of a hydrogen-transferring catalyst, to an aniline of the formula I.

A third advantageous modification of the process of the invention comprises a procedure whereby firstly an enamine of the formula II is reacted with an excess of acrolein unreacted acrolein, and solvent present are removed; and the resulting product is immediately reacted with an aqueous solution of an amine of the formula III in the presence of a hydrogen-transferring catalyst. In this modification, the excess acrolein can be up to 1.5 moles per mole of enamine of the formula II. The reaction is preferably performed in the absence of solvent.

It is advantageous to perform the final reaction with the amine of the formula III and dehydrogenation under pressure in the presence of an inert gas and/or of a hydrogen-acceptor. A suitable inert gas is, in particular, nitrogen, and suitable hydrogen-acceptor are, for example, olefins such as propylene, or carbonyl compounds such as acetone, methylethylketone, cyclohexanone or ketones formed during the reaction such as 2,6-dimethyl-cyclohexanone or 2,6-dimethylcyclohexenone. It is further advantageous to interrupt the dehydrogenation one or several times and to pass nitrogen through the reaction vessel in order to remove hydrogen and to carry out the dehydrogenation in the presence of nitrogen. The amount of inert gas is so regulated that there is created in the reaction vessel an initial pressure of 5 to 25 bars.

With carrying out of the final reaction with the amine of the formula III and dehydrogenation in an organic solvent, the final products of the formula I can be obtained, after separation of the catalyst, by evaporating off the solvent and processing the residue by distillation. With carrying out the final reaction with the amine of the formula III and dehydrogenation in an aqueous medium, the end products can be advantageously isolated from the reaction mixture by extraction with a suitable solvent, such as ether or methylene chloride. The final products of the formula I are then obtained from the extract by evaporating off the solvent and processing the residue by distillation.

The process of the invention is suitable for the production of 2,6-dimethylaniline and N-alkyl- or N-alkoxyalkyl-2,6-dimethylanilines. By virtue of the process according to the invention, there is provided a simple means of obtaining aniline derivatives of formula I from readily accessible aliphatic starting materials.

The process of the invention is further illustrated by the following Examples.

EXAMPLE 1

(a) 2,6-dimethyl-cyclohex-2-en-1-one 26.1 g (0.168 mole) of N-(3-pent-2-enyl)-morpholine is slowly added dropwise to a solution, cooled to 0°, of 16.8 g (0.3 mole) of freshly distilled acrolein in 150 ml of dioxane, with the temperature rising to 5° C. After completion of the addition, stirring is maintained for half an hour with ice-cooling, and the mixture is then allowed to stand overnight. The solvent is afterwards evaporated off and the oil obtained as residue is dissolved in 120 ml of 20% aqueous hydrochloric acid. On stirring of the acidified solution at room temperature, there precipitates an oil which, after one to two days' stirring, is taken up in ether. The aqueous phase is extracted a further five times with ether. The combined ether phases are dried over magnesium sulphate and the ether is distilled off. There is obtained 18.5 g of crude 2,6-dimethyl-cyclohex-2-en-1-one in the form of oil, which yields, after distillation in a water-jet vacuum, 15.0 g of 2,6-dimethyl-cyclohex-2-en-1-one (72% of theory); b.p. 62°-63° C./10 Torr.

The N-(3-pent-2-enyl)-morpholine used as starting material is produced as follows:

87.0 g (1 mole) of morpholine and 129.3 g (1.5 moles) of diethyl ketone are placed into a pear-shaped flask fitted with a Soxhlet attachment. The Soxhlet, in which there is provided a tube containing about 200 g of molecular sieve 4A, is then filled up to approximately half a centimetre from the overflow level with diethyl ketone. The contents of the flask are subsequently refluxed for 300 hours at a bath temperature of 150° C. After cooling, the combined liquids from Soxhlet and flask are concentrated at 40° C. bath temperature in a rotary evaporator. The oily residue is distilled in a water-jet vacuum to yield 84.8 g (55% of theory relative to the morpholine used) of N-3-pent-2-enyl)-morpholine; b.p. 88°-90° C./10 Torr.

(b) 2,6-dimethylaniline

A solution of 19.7 g (0.158 mole) of 2,6-dimethyl-cyclohex-2-en-1-one in 180 ml of conc. ammonia is heated, after the addition of 4.0 g of palladium on charcoal (5%), in a hydrogenating autoclave for 4 hours at 280°-290° C., whereby a pressure of 20 bars is established, and is then maintained under these conditions for 5 hours. Cooling and pressure release are then carried out; the contents are again heated for about 5 hours and the pressure is again released. In order to effect the complete removal of hydrogen, the procedure of heating and pressure release is carried out in all three times. An addition is then made of 150 ml of ether and the catalyst is filtered off. The filter residue is washed three times alternately with 100 ml of ether and water, respectively. The mother liquor is extracted, after separation of the ether phase, five times with 150 ml of ether each time. The combined ether phases are dried over magnesium sulphate. After the ether has been distilled off, there remains 17.0 g of crude 2,6-dimethylaniline, from which is obtained, by distillation in a water-jet vacuum, 12.0 g (63% of theory) of pure 2,6-dimethylaniline; b.p. 103° C./18 Torr.

EXAMPLE 2

2,6-Dimethyl-cyclohex-2-en-1-one 19.6 g (0.35 mole) of freshly distilled acrolein is added dropwise at a maximum of 50° C., with ice-cooling, to a solution of 27.8 g (0.2 mole) of N-(3-pent-2-enyl)-pyrrolidine in 50 ml of benzene. After completion of the addition, the mixture is stirred overnight at room temperature; it is subsequently heated for 2 hours at 50°-55° C. and then concentrated by evaporation. The oil remaining is dissolved in 250 ml of 20% hydrochloric acid and the solution is stirred overnight. Extraction is then performed five times with ether; the combined extracts are dried over magnesium sulphate and the ether is distilled off. The crude 2,6-dimethyl-cyclohex-2-en-1-one remaining is purified by vacuum distillation. There is obtained 14.8 g (60% of theory) of 2,6-dimethyl-cyclohex-2-en-1-one, b.p. 62°-64° C./10 Torr.

The N-(3-pent-2-enyl)-pyrrolidine used as starting material is produced as follows:

584 g of pyrrolidine and 126.7 g of diethyl ketone are placed into a pear-shaped flask fitted with a Soxhlet attachment. In the Soxhlet there is contained 200 g of molecular sieve A4. The mixture is boiled for 170 hours at 150° C. bath temperature, and subsequently concentrated in a rotary evaporator. The residue obtained is distilled in a water-jet vacuum. There is obtained 142 g (70% of theory) of N-(3-pent-2-enyl)-pyrrolidine, b.p. 80° C./18 Torr. With the use of excess diethyl ketone, it is possible to attain a yield of 94%.

EXAMPLE 3

(a) N-(2-Methoxyethyl)-2,6-dimethylcyclohex-2-en-1-one-imine 38.8 g (0.25 mole) of N-(3-pent-2-enyl)-morpholine is slowly added dropwise at 0° to a solution of 25.1 g (0.448 mole) of freshly distilled acrolein in 175 ml of dioxane, with the temperature rising to 5° C. After 16 hours' subsequent stirring, the solvent is evaporated off in vacuo. There remains 29.0 g of an oil which, after the addition of 37.5 g (0.5 mole) of 2-methoxyethylamine, is boiled for 30 hours at a bath temperature of 130° C. The mixture is afterwards distilled to yield 1.5 g of N-(2-methoxyethyl)-2,6-dimethyl-cyclohex-2-en-1-one-imine; b.p. 124° C./15 Torr (33% of theory).

(b) N-(2-methoxyethyl)-2,6-dimethylaniline 8.0 g of N-(2-methoxyethyl)-2,6-dimethylcyclohex-2-en-1-one-imine (0.0442 mole), 100 ml of dioxane, 40.0 g of propylene and 1.0 g of palladium on charcoal (5%) are heated in a hydrogenating autoclave for 24 hours at 120°–130° C. After cooling, the catalyst is filtered off and washed on the filter twice with ether. After concentration of the mother liquor by evaporation, there is obtained 6.6 g of crude N-(2-methoxyethyl)-2,6-dimethylaniline, which yields, by distillation in high vacuum, 3.5 g (45% of theory) of pure N-(2-methoxyethyl)-2,6-dimethylaniline; b.p. 49° C./0.1 Torr.

EXAMPLE 4

N-(2-Methoxyethyl)-2,6-dimethylaniline 2.0 g (0.0161 mole) of 2,6-dimethyl-cyclohex-2-en-1-one, 50 ml of toluene, 1.8 g (0.024 mole) of 2-methoxyethylamine and 0.5 g of palladium on charcoal (5%) are heated with a starting pressure of 17 bars (7 bars propylene and 10 bars nitrogen) for 10 hours at 180° C. After cooling, the catalyst is filtered off and the filter residue is washed with ether and toluene. The solvent is evaporated off to leave 1.0 g of crude N-(2-methoxyethyl)-2,6-dimethylaniline, from which is obtained, by distillation in high vacuum, 0.4 g (13% of theory) of pure N-(2-methoxyethyl)-2,6-dimethylaniline; b.p. 61°–62° C./0.1 Torr.

EXAMPLE 5

2,6-Dimethylaniline 15.1 g (0.093 mole) of N-(3-pent-2-enyl)-morpholine is slowly added dropwise to 9.75 g (0.174 mole) of freshly distilled acrolein with ice-cooling being applied; there occurs a temperature rise from 10° C. initially to 110° C. After completion of the addition, stirring is maintained for 15 hours and the excess acrolein is afterwards distilled off. There remain behind 20.0 g of an oil, which is heated with 150 ml of concentrated aqueous ammonia and 4.0 g of palladium on charcoal (5%) at a pressure of 20 bars (nitrogen) for 24 hours at 280°–290° C.; heating is carried out firstly for about 5 hours with subsequent cooling and exhausting and reheating; cooling, exhausting and reheating are subsequently performed every 5 hours. An addition of 300 ml of ether is then made to the mixture and the catalyst is filtered off. The filter residue is washed four times with 100 ml of ether each time. After separation of the ether pulse from the mother liquor, the aqueous phase is extracted five times with 150 ml of ether each time; the combined ether extracts are dried over magnesium sulphate and the ether is distilled off. The resulting crude 2,6-dimethylaniline is purified by vacuum distillation to yield 4.2 g (35% of theory) of 2,6-dimethylaniline; b.p. 103° C./18 Torr.

EXAMPLE 6

2,6-Dimethylaniline 12.9 g (0.23 mole) of freshly distilled acrolein is added dropwise at room temperature to a solution of 27.8 g (0.2 mole) of N-(3-pent-2-enyl)-pyrrolidine in 50 ml of absolute benzene, with the temperature rising to a maximum of 50° C. After completion of the addition, the mixture is stirred for 2 hours at room temperature. It is subsequently boiled for 15 hours at about 110° C. bath temperature in a water-separator. The oil obtained after evaporating off the solvent is heated for 18 hours with 100 ml of abs. dioxane, 10.0 g of ammonia, 50.0 g of propylene and 5.0 g of palladium on charcoal (5%) at 120°–130° C. under a pressure of 47 bars (nitrogen). After the addition of 100 ml of ether, the catalyst is filtered off and washed three times with ether. The oil obtained after removal of the solvent by evaporation is distilled in vacuo. There is obtained 4.5 g (20% of theory) of 2,6-dimethylaniline, b.p. 103° C./18 Torr, and as byproducts 1.9 g (8% of theory) of 2,6-dimethyl-cyclohex-2-en-1-one, b.p. 62°–64° C./17 Torr, and 2.4 g (10% of theory) of 2,6-dimethyl-cyclohexanone.

EXAMPLE 7

2,6-Dimethylaniline 14.0 g (0.25 mol) of acrolein is added dropwise at 25° to 30° C. to 23.3 g (0.15 mol) of N-(3-penten-2-yl)-morpholine. The mixture obtained is stirred for 15 hours at 25° C. and subsequently, for further 15 hours at 50° C. Then the mixture is transferred into an autoclave and after addition of 400 ml of a 40% by weight aqueous solution of methylamine and 10.0 g of palladium coal (5%), the whole is heated under a nitrogen pressure of 50 bar for 5 hours at 280° to 290° C. Subsequently the catalyst is separated off by filtration and washed with ether. The filtrate is several times extracted with ether, the combined extracts are dried over magnesium sulphate and the ether is distilled off. Then water is added to the residue and the whole is acidified by addition of hydrochloric acid. The acid solution obtained is extracted with ether and the extract is discarded. Now sodium bicarbonate is added to the acid solution until the mixture shows alkaline reaction and the whole is again extracted with ether. The extract is dried over sodium sulphate and the ether is distilled off. N-methyl-2,6-dimethylaniline is obtained by distillation of the residue at 0.1 Torr.

EXAMPLE 8

2,6-Dimethylaniline 8.4 g (0.15 mol) of acrolein is added dropwise to a solution of 23.3 g (0.15 mol) of N-(3-penten-2-yl)-morpholine in 100 ml of methylene chloride. After addition of the acrolein the mixture is stirred for 15 hours at 25° C. and subsequently for further 15 hours at 50° C. Then 12.0 g (0.225 Mol) of ammonium chloride are added and the solvent is distilled off. The residue is transferred into an autoclave and after addition of 400 ml of concentrate aqueous ammonia and 10.0 g of palladium coal (5%) the whole is heated under a nitrogen pressure of 50 bar for 15 hours at 280°–290° C. Then the catalyst is filtered off and washed with ether. The filtrate is extracted several times with ether. The extracts are combined and dried over magnesium sulphate and the ether is distilled off. The residue (14.2 g; 79% of theory) is distilled at a pressure of 15 torr. There is obtained 6.7 g (37% of theory) of 2,6-dimethylaniline, b.p. 15: 94°–98° C.

The fraction boiling between 60° and 90° C. contains 2,6-dimethylcyclohexanone and 2,6-dimethylcyclohexenone. After addition of ammonia and a dehydrogenation catalyst these products can be converted into 2,6-dimethylaniline, as described above. The morpholine which is also present in the fraction boiling between 60° and 90° C. can be reused for the preparation of N-(3-penten-2-yl)-morpholine.

EXAMPLE 9

N-(2'-Methoxyethyl)-2,6-dimethylaniline 14.0 g (0.25 mol) of acrolein is added dropwise at a maximal temperature of 35° C. to a solution of 23.3 g (0.15 mol) of N-(3-penten-2-yl)-morpholine in 100 ml of abs. dioxane. The mixture obtained is stirred for 15 hours at 25° C. and thereafter for further 15 hours at 50° C. The solvent is distilled off and the residue is transferred into an autoclave and, after addition of a solution of 200 ml of 2-methoxyethylamine in 200 ml of water and 10.0 g of palladium coal (5%) the whole is heated under a nitrogen pressure of 50 bar for 11 hours at 280°–290° C. Then the catalyst is separated by filtration and washed with ether. After separation of the etheral layer the filtrate is extracted several times with ether. The extracts are combined and dried over magnesium sulphate and the ether is distilled off. The residue is distilled in vacuo. The fraction boiling between 30° and 63° C. at 0.4 torr is mixed with water and acidified by addition of hydrochloric acid. The resulting solution is extracted with ether and the extract is discarded. Subsequently sodium bicarbonate is added to the aqueous solution until an alkaline reaction is reached and the whole is again extracted several times with ether. The extracts are combined and dried over magnesium sulphate and the ether is evaporated. N-(2-methoxyethyl)-2,6-dimethylaniline is obtained as an oily residue.

EXAMPLE 10

N-(2'-Methoxyethyl)-2,6-dimethylaniline 14.0 g (0.25 mol) of acrolein is added dropwise to a solution of 23.3 g (0.15 mol) of N-(3-penten-2-yl)-morpholine in 100 ml of chloroform. The mixture obtained is stirred for 15 hours at room temperature and then for further 15 hours at 50° C. Thereafter the solvent is distilled off and the residue is transferred into an autoclave and, after addition of a solution of 200 ml of 2-methoxyethylamine in 200 ml of benzene and 10.0 g of paladium coal (5%) the whole is heated under a nitrogen pressure of 50 bar for 15 hours at 280°–290° C. Then the solvent is evaporated and water is added to the residue. The whole is acidified by addition of hydrochloric acid. The solution obtained is extracted with ether and the extract is discarded. Subsequently sodium bicarbonate is added to the aqueous solution until alcaline reaction is reached and the whole is again several times extracted with ether. The extracts are combined and dried over magnesium sulphate and the ether is distilled off. The residue (40.1 g) is distilled in vacuo at 0.4 torr. There is obtained 7.5 g (28% of theory) of N-(2'-methoxyethyl)-2,6-dimethylaniline.

EXAMPLE 11

2,6-Dimethylaniline 14.0 g (0.25 mol) of acrolein is added dropwise at maximal temperature of 40° C. to a solution of 23.3 g (0.15 mol) of N-(2-penten-2-yl)-morpholine in 100 ml of abs. chloroform. The mixture is stirred for 15 hours at 25° C. and then for further 15 hours at 50° C. Thereafter the solvent is distilled off and the residue is transferred into an autoclave and, after addition of 400 ml concentrated aqueous ammonia and 10.0 g of paladium coal (5%) the whole is heated under a nitrogen pressure of 50 bar for 15 hours at 280° to 290° C. Subsequently the catalyst is separated by filtration and washed with ether. After separation of the etheral layer the filtrate is several times extracted with ether. The extracts are combined and dried over magnesium sulphate and the ether is distilled off. The residue (22 g) is distilled in vacuo. There is obtained 6.5 g (35% of theory) of 2,6-dimethylaniline, b.p. 15: 94°–96° C.

I claim:

1. Process for the production of aniline derivatives of the formula I

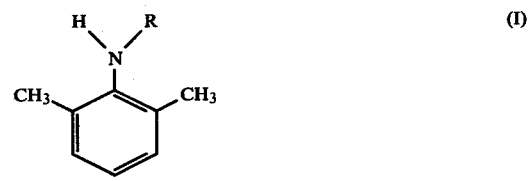

wherein
R represents hydrogen, $C_1$–$C_4$-alkyl or $C_1$–$C_4$-alkyl substituted by $C_1$–$C_2$-alkoxy,
in which process an enamine of the formula II

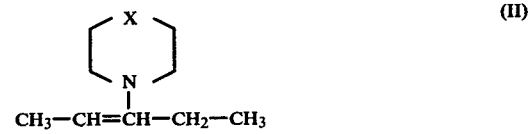

wherein X represents a methylene group, oxygen or a direct bond, is reacted at a temperature of between −30° C. and 150° C. with acrolein in the presence of an inert aprotic solvent, or in the absence of a solvent; and the reaction product obtained is subsequently heated to a temperature of between 100° and 400° C. in the presence of a hydrogen-transfer catalyst and in the presence of an amine of the formula III

wherein R has the meaning given under formula I.

2. Process according to claim 1 wherein the reaction with an amine of the formula III is performed in an aqueous medium or in the presence of an organic solvent.

3. Process according to claim 1 wherein an anhydrous acid or a salt of an amine of formula III is added to the reaction mixture after the reaction of an enamine of formula II with acrolein.

4. Process according to claim 1 wherein hydrogen chloride, sulphuric acid phosphoric acid, p-toluenesulfonic acid, methanesulfonic acid, III acid or a salt of the amine of formula II with one of the afore-mentioned acids is added to the reaction mixture after the reaction of an enamine of formula II with acrolein.

5. Process according to claim 1 wherein an enamine of the formula II is reacted with acrolein and the reaction product obtained is converted by the addition of an acid into 2,6-dimethyl-2-cyclohexen-1-one and this is subsequently converted with an amine of the formula III, in the presence of a hydrogen-transfer catalyst, into an aniline of the formula I.

6. Process according to claim 1 wherein the reaction product formed by reaction of an enamine of the formula II with acrolein is firstly reacted with an amine of the formula III, and the product formed is subsequently hydrogenated, in the presence of a hydrogen-transferring catalyst, to an aniline of the formula I.

7. Process according to claim 1 wherein an enamine of the formula II is reacted with an excess of acrolein unreacted acrolein and solvent present are removed; and the resulting product is immediately reacted with an aqueous solution of an amine of the formula III, in the presence of a hydrogen-transfer catalyst, to an aniline of the formula I.

8. Process according to claim 1 wherein the final reaction with the amine of the formula III and dehydrogenation are performed under pressure in the presence of an inert gas and/or in the presence of a hydrogen-transfer catalyst.

* * * * *